United States Patent
Learmonth et al.

(10) Patent No.: US 8,524,746 B2
(45) Date of Patent: Sep. 3, 2013

(54) DOSAGE REGIMEN FOR COMT INHIBITORS

(75) Inventors: David Alexander Learmonth, S. Mamede do Coronado (PT); Laszlo Erno Kiss, S. Mamede do Coronado (PT); Pedro Nuno Leal Palma, S. Mamede do Coronado (PT); Humberto dos Santos Ferreira, S. Mamede do Coronado (PT); Patricio Manuel Vieira Araujo Soares da Silva, S. Mamede do Coronado (PT)

(73) Assignee: Bial-Portela & Ca., S.A., S. Mamede do Coronado (PT)

( * ) Notice: Subject to any disclaimer, the term of this patent is extended or adjusted under 35 U.S.C. 154(b) by 480 days.

(21) Appl. No.: 12/524,848

(22) PCT Filed: Oct. 10, 2007

(86) PCT No.: PCT/PT2007/000043
§ 371 (c)(1),
(2), (4) Date: Dec. 30, 2009

(87) PCT Pub. No.: WO2008/094053
PCT Pub. Date: Aug. 7, 2008

(65) Prior Publication Data
US 2010/0113529 A1    May 6, 2010

(30) Foreign Application Priority Data
Jan. 31, 2007   (EP) .................................. 07002091

(51) Int. Cl.
*A61K 31/4439* (2006.01)
*A61P 25/00* (2006.01)
*A61P 25/16* (2006.01)
*A61P 25/18* (2006.01)
*C07D 413/04* (2006.01)

(52) U.S. Cl.
USPC ...................................... 514/340; 546/269.4

(58) Field of Classification Search
USPC ...................................... 514/340; 546/269.4
See application file for complete search history.

(56) References Cited

U.S. PATENT DOCUMENTS

| | | |
|---|---|---|
| 1,532,178 A | 4/1925 | Godbold |
| 3,647,809 A | 3/1972 | Reiter et al. |
| 4,065,563 A | 12/1977 | Narayanan et al. |
| 4,386,668 A | 6/1983 | Parish |
| 4,963,590 A | 10/1990 | Backstrom et al. |
| 5,236,952 A | 8/1993 | Bernauer et al. |
| 5,476,875 A | 12/1995 | Bernauer et al. |
| 5,633,371 A * | 5/1997 | Bernauer et al. ............. 544/105 |
| 5,705,703 A | 1/1998 | Bernauer et al. |
| 6,206,110 B1 | 3/2001 | Slaughter et al. |
| 6,509,363 B2 | 1/2003 | Salituro et al. |
| 6,512,136 B1 | 1/2003 | Benes et al. |
| 6,660,753 B2 | 12/2003 | Van Wagenen et al. |
| 7,041,685 B2 | 5/2006 | Cai et al. |
| 7,112,595 B2 | 9/2006 | Wagenen et al. |
| 7,144,876 B2 | 12/2006 | Cai et al. |
| 7,317,029 B2 | 1/2008 | Cai et al. |
| 7,435,750 B2 | 10/2008 | Cai et al. |
| 7,553,964 B2 | 6/2009 | Liu et al. |
| 2003/0055085 A1 | 3/2003 | Wagenen et al. |
| 2004/0097555 A1 | 5/2004 | Ohkawa et al. |
| 2006/0019956 A1 | 1/2006 | Green |
| 2006/0160812 A1 | 7/2006 | Schubert et al. |
| 2007/0048384 A1 | 3/2007 | Rosenberg et al. |
| 2007/0078133 A1 | 4/2007 | Liu et al. |

(Continued)

FOREIGN PATENT DOCUMENTS

| | | |
|---|---|---|
| EP | 1 845 097 | 10/2007 |
| EP | 1 881 979 | 8/2010 |

(Continued)

OTHER PUBLICATIONS

Howse (Brocresine in Parkinson's disease, Action of a peripheral and central decarboxylase inhibitor in potentiating levodopa, Journal of Neurology, Neurosurgery, and Psychiatry, 1973, 36, pp. 27-29).*
U.S. Appl. No. 13/002,287, filed Jul. 29, 2009, de Almeida.
Nutt, J.G., "Catechol-O-methyltransferase inhibitors for treatment of Parkinson's disease", *The Lancet*, (1998), vol. 351, pp. 1221-1222.
Nutt, J.G. et al., "Pharmacokinetics of Levodopa", *Clinical Neuropharmacology*, (1984), vol. 7, No. 1, pp. 35-49.
Parashos, S.A. et al., "Frequency, Reasons, and Risk Factors of Entacapone Discontinuation in Parkinson Disease", *Clin. Neuropharmacol*, (2004), vol. 27, No. 3, pp. 119-123.
Poulain, R. F. et al., "Parallel synthesis of 1,2,4-oxadiazoles from carboxylic acids using an improved, uranium-based, activation," Tetrahedron Letters 42:1495-1498 (2001).

(Continued)

*Primary Examiner* — San-Ming Hui
*Assistant Examiner* — Kathrien Cruz
(74) *Attorney, Agent, or Firm* — McCarter & English, LLP; Steven G. Davis; Wei Song

(57) ABSTRACT

The invention relates to the use of an oxodiazolyl compound (I) for the preparation of a medicament for the prevention or treatment of central and peripheral nervous system associated disorders, wherein said medicament is administered according to a dosing regimen having a dosing periodicity ranging from about twice a day to about once every other day.

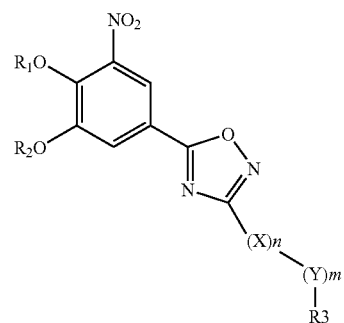

17 Claims, 3 Drawing Sheets

(56) References Cited

U.S. PATENT DOCUMENTS

| | | |
|---|---|---|
| 2007/0219187 A1 | 9/2007 | Bessis et al. |
| 2008/0051441 A1 | 2/2008 | Brown et al. |
| 2008/0167286 A1 | 7/2008 | Gopalakrishnan et al. |
| 2008/0269236 A1 | 10/2008 | Ji et al. |
| 2009/0054437 A1 | 2/2009 | Learmonth et al. |
| 2009/0111778 A1 | 4/2009 | Apodaca et al. |
| 2009/0162283 A1 | 6/2009 | Bando et al. |
| 2009/0227626 A1 | 9/2009 | Deraeve et al. |
| 2009/0312347 A1 | 12/2009 | Dahl et al. |
| 2010/0004284 A1 | 1/2010 | Farina et al. |
| 2010/0113529 A1 | 5/2010 | Learmonth et al. |
| 2010/0168113 A1 | 7/2010 | Learmonth et al. |
| 2011/0014282 A1 | 1/2011 | de Vasconcelos |

FOREIGN PATENT DOCUMENTS

| | | |
|---|---|---|
| WO | 93/13083 A1 | 7/1993 |
| WO | WO-01/12627 | 2/2001 |
| WO | 01/68083 A1 | 9/2001 |
| WO | WO-02/17175 | 2/2002 |
| WO | 02/068417 A2 | 9/2002 |
| WO | WO-02/068417 | 9/2002 |
| WO | 02/100826 A2 | 12/2002 |
| WO | 2002/096867 A2 | 12/2002 |
| WO | WO-2005/013982 | 2/2005 |
| WO | WO-2005/044797 | 5/2005 |
| WO | WO-2006/114400 | 11/2006 |
| WO | WO-2006/129199 | 12/2006 |
| WO | WO-2006-132914 | 12/2006 |
| WO | WO 2007/013830 A1 | 2/2007 |
| WO | WO-2007/113276 | 10/2007 |
| WO | WO 2007/117165 A1 | 10/2007 |
| WO | WO-2008/021388 | 2/2008 |
| WO | WO-2008/094053 | 8/2008 |
| WO | WO-2009/029632 | 3/2009 |

OTHER PUBLICATIONS

Reches, A. et al., "3-$O$-Methyldopa inhibits rotations induced by levodopa in rats after unilateral destruction of the nigrostriatal pathway", *Neurology*, (1982), vol. 32, No. 8, pp. 887-888.

Soares-da-Silva, P. et al., "The $O$-methylated derivative of $_L$-DOPA, 3-$O$-methyl-$_L$-DOPA, fails to inhibit neuronal and non-neuronal aromatic L-amino acid decarboxylase", *Brain Research*, (2000), 863. pp. 293-297.

Smith, K.S. et al., "In Vitro Metabolism of Tolcapone to Reactive Intermediates: Relevance to Tolcapone Liver Toxicity" *Chem. Res. Toxicol.*, (2003), vol. 16, pp. 123-128.

Tohgi, H. et al., "The Significance of 3-$O$-methyldopa concentrations in the cerebrospinal fluid in the pathogenesis of wearing-off phenomenon in Parkinson's disease", *Neurosci. Letters*, (1991) 132, pp. 19-22.

International Search Report for Application No. PCT/PT2007/000043 date of mailing Apr. 23, 2008.

\* cited by examiner

DOSAGE REGIMEN FOR COMT INHIBITORS

CROSS REFERENCE TO RELATED APPLICATIONS

This application is a National Stage Application of PCT/PT2007/000043, filed Oct. 10, 2007, which claims the benefit of European Application No. 07002091,2, filed Jan. 31, 2007. The contents of both of these applications are incorporated by reference herein in their entirety.

This invention relates to novel substituted nitrocatechols and to their use in the treatment of central and peripheral nervous system disorders according to a specified dosing regimen.

The rationale for the use of COMT inhibitors as adjuncts to L-DOPA/AADC therapy is based on their ability to reduce metabolic O-methylation of L-DOPA to 3-O-methyl-L-DOPA (3-OMD). The duration of L-DOPA induced clinical improvement is brief as a result of the short in vivo half-life of L-DOPA which contrasts with the long half-life of 3-OMD. Additionally, 3-OMD competes with L-DOPA for transport across the blood-brain barrier (BBB), which means that only a very limited amount of an orally administered dose of L-DOPA actually reaches the site of action, i.e. the brain. Commonly, within only a few years of starting L-DOPA therapy with the usual dosage regime, L-DOPA induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters; 132:19-22, 1992). It has been speculated that this may result from impaired brain penetration of L-DOPA due to competition for the transport system across the BBB with 3-OMD (Reches, A. et al., Neurology, 32:887-888, 1982) or more simply that there is less L-DOPA available to reach the brain (Nutt, J. G., Fellman, J. H., Clin. Neuropharmacol., 7:35-49, 1984). In effect, COMT inhibition protects L-DOPA from metabolic breakdown in the periphery through O-methylation, such that with repeated doses of L-DOPA, the mean plasma L-DOPA concentration is raised. In addition to reduced competition for transport into the brain, a significantly greater percentage of the orally administered dose of L-DOPA is able to reach the site of action. Thus COMT inhibition serves to increase the bioavailability of L-DOPA and the duration of antiparkinsonian action is prolonged with single doses of L-DOPA (Nutt, J. G., Lancet, 351:1221-1222, 1998).

The most potent COMT inhibitors thus far reported are 3,4-dihydroxy-4'-methyl-5-nitrobenzophenone (Tolcapone, Australian pat. AU-B-69764/87) and (E)-2-cyano-N,N-diethyl-3-(3,4-dihydroxy-5-nitrophenyl)acrylamide (Entacapone, German pat. DE 3740383 A1).

Although sharing essentially the same pharmacophore, tolcapone differs from entacapone in that it easily enters the central nervous systems (CNS) and is able to inhibit cerebral COMT as well as peripheral COMT. However, shortly after its launch, tolcapone was withdrawn from the market after several cases of hepatotoxicity were reported including three unfortunate deaths from fatal fulminant hepatitis. Today tolcapone can only be used in Parkinsonian patients who are unresponsive to other treatments and strictly only with regular monitoring of liver function, which is expensive and inconvenient for the patient. Although the actual mechanistic causes of the liver toxicity associated with tolcapone are not fully understood, in vitro studies have shown that tolcapone may be reduced metabolically to reactive intermediates and it has been speculated that these may form covalent adducts with hepatic proteins resulting in hepatocellular injury (Smith, K. S. et al, Chem. Res. Toxicol., 16:123-128, 2003).

Entacapone on the other hand, although sharing the same nitrocatechol pharmacophore with tolcapone, is not associated with liver toxicity and is generally regarded as a safe drug.

Unfortunately however, entacapone is a significantly less potent COMT inhibitor than tolcapone and has a much shorter in-vivo half-life. This means that entacapone has a very limited duration of effect and as a consequence, the drug must be administered in very high doses with every dose of L-DOPA taken by the patient. As such, the clinical efficacy of entacapone has been questioned—indeed a recent study (Parashos, S. A. et al., Clin. Neuropharmacol., 27(3): 119-123, 2004) revealed that the principal reason for discontinuation of entacapone treatment in Parkinson's disease patients was a perceived lack of efficacy.

Furthermore, the relatively short in-vivo half-life of known COMT inhibitors requires continuous treatment regimens normally involving the administration of several doses a day which many patients find to be burdensome. For example, tolcapone has to be administered three times a day. This factor can therefore interfere with patient compliance and quality of life.

Accordingly, there is still a need for COMT inhibitors exhibiting balanced properties of bioactivity, bioavailability and safety. In particular, there is a need for COMT inhibitors having a long in-vivo half-life and, thus, a prolonged action on COMT enabling fewer dosages to obtain the desired therapeutic effect.

We have now surprisingly found that compounds of general formula I are very potent COMT inhibitors which are also endowed with exceptionally long duration of action compared to COMT inhibitors in the prior art.

We have further surprisingly found that compounds of general formula I markedly enhance the bioavailability of L-DOPA and increase the delivery of L-DOPA to the brain. The compounds significantly augment the levels of dopamine in the brain.

Even more surprisingly, the increased levels of L-DOPA are maintained steady over a twenty-four hour period. These effects upon both COMT activity and L-DOPA bioavailability at 24 h after the administration of compounds of general formula I are markedly greater than those observed with tolcapone, the only COMT inhibitor thus far known to be endowed with a reasonably long duration of action. At shorter time points (2 and 7 h) compounds of general formula I produce increases in L-DOPA delivery to the brain similar to those observed at 24 h, which contrasts to that observed with tolcapone. This results in a more steady delivery of L-DOPA to the brain after the administration of compounds of general formula I, whereas tolcapone is prone to induce marked oscillations in the brain delivery of L-DOPA. Thus compounds of general formula I are more likely to be endowed with therapeutic advantages due to sustained constant elevation of L-DOPA levels whilst the use of tolcapone is likely to induce undesirable side-effects such as dyskinesia due to abrupt increases and decreases in L-DOPA levels.

Compounds of general formula I are compounds having the following formula

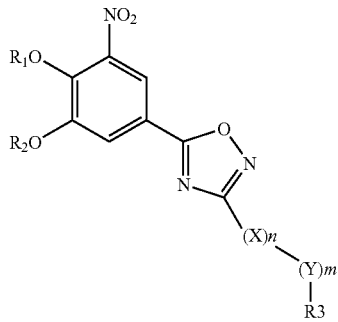

where $R_1$ and $R_2$ are independently from each other hydrogen or a group which is hydrolysable under physiological conditions, optionally substituted lower alkanoyl or aroyl; X represents a methylene group; Y represents an atom of oxygen, nitrogen or sulphur; n represents the number 0, 1, 2 or 3 and m represents the number 0 or 1; $R_3$ represents a pyridine N-oxide group according to the formula A, B or C, which is connected as indicated by the unmarked bond:

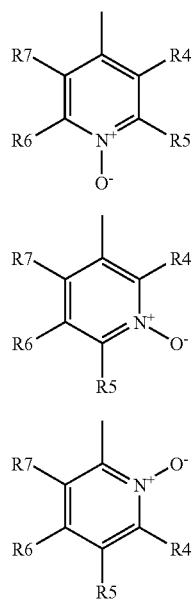

where $R_4$, $R_5$, $R_6$ and $R_7$ are the same or different, and signify hydrogen, lower alkyl, lower thioalkyl, lower alkoxy, aryloxy or thioaryl group, lower alkanoyl or aroyl group, optionally substituted aryl group, amino, lower alkylamino, lower dialkylamino cycloalkylamino or heterocycloalkylamino group, lower alkylsulphonyl or arylsulphonyl group, halogen; haloalkyl, trifluoromethyl, cyano, nitro or heteroaryl group, or taken together signify aliphatic or heteroaliphatic rings or aromatic or heteroaromatic rings; the term alkyl means carbon chains, straight or branched, containing from one to six carbon atoms; the term aryl means a phenyl or naphthyl group, optionally substituted by alkoxy or halogen groups; the term heterocycloalkyl represents a four to eight-membered cyclic ring optionally incorporating other atoms of oxygen, sulphur or nitrogen; the term heteroaryl represents a five or six-membered ring incorporating an atom of sulphur, oxygen or nitrogen; the term halogen represents fluorine, chlorine bromine or iodine.

Preferably, in the above formula, $R_4$, $R_5$, $R_6$ and $R_7$ independently from each other represent hydrogen, $C_1$-$C_6$-alkyl, $C_1$-$C_6$-thioalkyl, $C_1$-$C_6$-alkoxy, $C_6$-$C_{12}$-aryloxy or a $C_6$-$C_{12}$-thioaryl group, $C_1$-$C_6$-alkanoyl or $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or two or more of residues $R_4$, $R_5$, $R_6$ and $R_7$ taken together represent aliphatic or heteroaliphatic rings or aromatic or heteroaromatic rings.

Preferably, $C_1$-$C_6$-alkyl residues represent methyl, ethyl, n-propyl, isopropyl, n-butyl, sec-butyl, tert-butyl, heptyl or hexyl. Preferably, $C_1$-$C_6$-thioalkyl residues represent thiomethyl, thioethyl, thio-n-propyl and thio-isopropyl and thio-n-butyl. Preferably, $C_1$-$C_6$-alkoxy residues represent methoxy, ethoxy, n-propoxy, isopropoxy, n-butoxy, sec-butoxy and tert-butoxy. Preferably, $C_6$-$C_{12}$-aryloxy residues represent phenoxy or naphthoxy which may optionally be substituted. Preferably, $C_6$-$C_{12}$-thioaryl residues represent thiophenyl and thionaphthyl which may optionally be substituted. Preferably, $C_1$-$C_6$-alkanoyl residues represent methanoyl, ethanoyl, propanoyl or butanoyl. Preferably, $C_7$-$C_{13}$-aroyl residues represent benzoyl and naphthoyl. Preferably, $C_1$-$C_6$—alkylamino residues represent methylamino, ethylamino, n-propylamino, isopropylamino and n-butylamino. Preferably, $C_1$-$C_6$-dialkylamino residues represent dimethylamino, diethylamino, di-n-propylamino, di-n-butylamino, di-isopropylamino, methylethylamino, methylpropylamino and ethylpropylamino. Preferably, $C_3$-$C_{12}$-cycloalkylamino residues represent pyrrolidino, piperidino, cyclohexylamino and dicyclohexylamino. Preferably, $C_3$-$C_{12}$-heterocycloalkylamino residues represent morpholino, 2,6-dimethylmorpholino, 3,5-dimethylmorpholino, piperazino, N-methylpiperazino and N-ethylpiperazino. Preferably, $C_1$-$C_6$-alkylsulphonyl or $C_6$-$C_{12}$-arylsulphonyl residues represent methylsulfonyl, ethylsulfonyl, phenylsulfonyl, and tolylsulfonyl. Preferably, halogen residues represent chloro, bromo, iodo and fluoro. Preferably, $C_1$-$C_6$-haloalkyl represents chloromethyl, fluoromethyl, dichloromethyl, difluoromethyl, trichloromethyl and trifluoromethyl. Preferably, heteroaryl residues represent pyridyl, pyrimidyl, isoxazolyl, oxazolyl, isoxadiazolyl, oxadiazolyl, triazolyl and tetrazolyl. In cases where two or more of residues $R_4$, $R_5$, $R_6$ and $R_7$ taken together represent aliphatic or heteroaliphatic rings or aromatic or heteroaromatic rings, preferred combined residues are indolizinyl, isoindolyl, indolyl, indazolyl, purinyl, quinolizinyl, naphthyridinyl, isoquinolyl and quinolyl. Preferably, n and m each signify the number 0 or 1, or both signify 0 or 1.

In the following description of medical indications, treatments and dosing regimens for pharmaceutical compositions containing compounds according to general formula I of the invention, the most preferred example of a compound according to the general formula I is 5-[3-(2,5-dichloro-4,6-dimethyl-1-oxy-pyridin-3-yl)-[1,2,4]oxadiazol-5-yl]-3-nitrobenzene-1,2-diol, henceforth designated as compound A, and its pharmacologically acceptable salts and esters.

Other preferred compounds of the above general formula (I) in the subsequent medical indications, treatments and dosing regimens include 3-(5-(3,4-dihydroxy-5-nitrophenyl)-1,2,4-oxadiazol-3-yl)-4-(trifluoromethyl)pyridine-1-oxide, 2-chloro-3-(5-(3,4-dihydroxy-5-nitrophenyl)-1,2,4-oxadiazol-3-yl)-4,6-dimethylpyridine-1-oxide, 3-(5-(3,4-dihydroxy-5-nitrophenyl)-1,2,4-oxadiazol-3-yl)-2-methyl-6-(trifluoromethyl)pyridine-1-oxide, 5-(5-(3,4-dihydroxy-5-nitrophenyl)-1,2,4-oxadiazol-3-yl)-2-(trifluoromethyl)pyridine-1-oxide, 5-(5-(3,4-dihydroxy-5-nitrophenyl)-1,2,4-oxadiazol-3-yl)-2-methyl-4-(trifluoromethyl)pyridine-1-oxide, 3-(5-(3,4-dihydroxy-5-nitrophenyl)-1,2,4-oxadiazol-3-yl)-2,6-dimethyl-4-(trifluoromethyl)pyridine-1-oxide, 3,5-dichloro-4-(5-(3,4-dihydroxy-5-nitrophenyl)-1,2,4-oxadiazol-3-yl)pyridine-1-oxide, 3-(5-(3,4-dihydroxy-5-nitrophenyl)-1,2,4-oxadiazol-3-yl)-6-methyl-2-phenyl-4-(trifluoromethyl)pyridine-1-oxide, 2-bromo-3-(5-(3,4-dihydroxy-5-nitrophenyl)-1,2,4-oxadiazol-3-yl)-4,5,6-trimethylpyridine-1-oxide, 2-chloro-3-(5-(3,4-dihydroxy-5-nitrophenyl)-1,2,4-oxadiazol-3-yl)-4,5,6-trimethylpyridine-1-oxide, 3-(5-(3,4-dihydroxy-5-nitrophenyl)-1,2,4-oxadiazol-3-yl)-2-(trifluoromethyl)pyridine-1-oxide, 2-chloro-3-(5-(3,4-dihydroxy-5-nitrophenyl)-1,2,4-oxadiazol-3-yl)-6-methylpyridine 1-oxide, 2-bromo-3-(5-(3,4-dihydroxy-5-nitrophenyl)-1,2,4-oxadiazol-3-yl)-6-methylpyridine-1-oxide, 2-bromo-5-chloro-3-(5-(3,4-dihydroxy-5-nitrophenyl)-1,2,4-oxadiazol-3-yl)-4,6-dimethylpyridine-1-oxide 5-[3-(2-chloro-1-oxy-pyridin-4-yl)-[1,2,4]oxadiazol-5-yl]-3-nitro-benzene-1,2-diol, 5-[3-(2-morpholin-4-yl-1-oxy-pyridine-4-yl)-[1,2,4]oxadiazol-5-yl]-3-nitro-benzene-1,2-diol, 5-[3-(4-bromo-1-oxy-pyridin-3-yl)-[1,2,4]oxadiazol-5-yl]-3-nitro-benzene-1,2-diol, 5-[3-(2-morpholin-4-yl-1-oxy-pyridin-3-yl)-[1,2,4]oxadiazol-5-yl]-3-nitro-benzene-1,2-diol, 5-[3-(2-methyl-1-oxy-6-phenyl-4-trifluoromethyl-pyridin-3-yl)-[1,2,4]oxadiazol-5-yl]-3-nitro-benzene-1,2-diol and 5-[3-(2-bromo-4,6-dimethyl-1-oxy-pyridin-3-yl)-[1,2,4]oxadiazol-5-yl]-3-nitro-benzene-1,2-diol and their pharmacologically acceptable salts and esters.

The present invention relates to the use of the compounds of general formula I, their pharmaceutically acceptable salts or esters for the prevention or treatment of certain pathological states, especially in humans, (e.g. central and peripheral nervous system disorders) and to preparation of pharmaceutical compositions containing them.

Preferably, the treated pathological states are central and peripheral nervous system associated disorders of humans. Preferred disorders include movement disorders and schizoaffective disorders. Movement disorders are characterised by either a lack of movement or excessive movement. Movement disorders preferably treated by compounds of general formula I include Parkinson disease, dystonia, dyskinesia, extrapyrimidal syndromes, gait, tremor, chorea, ballism, akathisia, athetosis, bradykinesia, freezing, rigidity, postural instability, myoclonus, and tics or Tourette syndrome. The most preferred disorder is Parkinson's Disease.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects. Treatment may prevent or delay the onset, retard the progression or ameliorate the symptoms of the disease or condition.

The compounds of the general formula I are preferably used for the preparation of a medicament for the prevention or treatment of central and peripheral nervous system associated disorders according to a specified dosing regimen.

Suitable dosing regimens comprise regimens having a dosing periodicity ranging from about twice a day to about once every other day.

As used herein, the term dosing periodicity refers to the number of effective doses of a compound of general formula I given in the specified time interval.

Preferably, the dosing periodicity is selected from twice per day, once per day and once every other day.

In case of a dosage periodicity of twice daily, the effects of the invention may be achieved by administration once in each 12 hour period even where the time between administrations (or dosing interval) is not 12 hours. The doses are preferably administered in dosing intervals of 8 to 16 hours, more preferably 12 hours, wherein two dosing intervals preferably accumulate to about 24 hours. Suitable non-limiting starting points for dosing intervals comprise the morning, mid-day, noon, afternoon, evening, and midnight. For example, a twice daily dosing regimen according to the invention can require the administration of a dose at 8.00 in the morning and another dose at 17.00 in the afternoon (in this case, the dosing intervals are 11 hours and 13 hours and add up to about 24 hours). Preferably, the time interval between two doses is about 12 h.

In case of a dosage periodicity of once daily, the effects of the invention may be achieved by administration once in each 24 hour period even when the time between administrations is not 24 hours. The doses are preferably administered in dosing intervals of about 24 hours. Suitable non-limiting starting points for dosing intervals comprise the morning, mid-day, noon, afternoon, evening, and midnight. For example, a once daily dosing regimen according to the invention can require the administration of a dose at 8.00 in the morning and another dose at 8.00 on the morning of the following day (in this case, the dosing interval is about 24 h).

In case of a dosage periodicity of once every other day, the effects of the invention can be achieved by administration once in each 48 hour period even where the time between administrations is not 48 hours. The doses are preferably administered in dosing intervals of 36 to 60 hours, wherein the dosing intervals preferably average about 48 hours. Suitable non-limiting starting points for dosing intervals comprise the morning, mid-day, noon, afternoon, evening, and midnight. For example, a once every other day dosing regimen according to the invention can require the administration of a dose at 8.00 in the morning on the first day and another dose at 13.00 in the afternoon of the third day (in this case, the dosing interval is 53 hours). Preferably, the time between each administration is about 48 h.

In the present invention, effective daily doses of compounds of general formula I are in the range of 1-1000 mg/day, more preferably 2 to 500 mg/day, even more preferably 3 to 250 mg/day, and most preferably 5-100 mg/day.

It is preferred that individual dosage units of compounds of general formula I are in the range of 1-500 mg, more preferably 2 to 300 mg/day, even more preferably 3 to 100 mg/day, and most preferably 5-50 mg, wherein the daily dosage can differ depending on the time of administration. For instance, in a twice daily dosing regimen, it is possible to administer a dose containing $11/24$ of the daily dose of a compound of general formula I at 8.00 in the morning and another dose containing $13/24$ of the daily dose of a compound of general formula I at 17.00 in the afternoon.

As used herein, the term "dosage unit" refers to the individual pharmaceutical formulation, e.g. a tablet, containing the compound of general formula I to be administered to a patient at that time of the dosage regimen.

Preferably the subject being treated with the compound of general formula I is also receiving therapy with L-DOPA and/or an aromatic L-amino acid decarboxylase inhibitor (AADC).

Suitable AADC include carbidopa and benserazide.

The compounds of general formula I, L-DOPA and AADC may be administered separately or in any combination. They may be administered concomitantly (for example, simultaneously) or sequentially and with the same or differing dosing periodicity. For example, the compounds of the general formula I can be concomitantly or sequentially administered with L-DOPA. In case of concomitant administration it is also possible to combine both active ingredients in one pharmaceutical formulation.

According to another aspect of the present invention there is provided a method of treating at least one condition or disease in a patient in need thereof comprising administering about twice per day to about once every other day a pharmacologically effective dose of a compound of general formula I as defined above to the patient.

Preferably the administration is once per day for all embodiments of the invention.

Preferably in all methods of the invention the subject being treated with the compound of general formula I is also receiving therapy with L-DOPA and/or an aromatic L-amino acid decarboxylase inhibitor (AADC).

According to another aspect of the invention there is provided a method for reducing COMT inhibition in a subject over 24 to 48 hours, comprising administering, about twice per day to about once every other day, an effective dose of a compound of general formula I as defined above to the subject.

According to another aspect of the invention there is provided a method for increasing levels of L-DOPA in the brain of a subject over 24 to 48 hours, comprising administering, about twice per day to about once every other day, an effective dose of a compound of general formula I as defined above to the subject.

According to another aspect of the invention there is provided a method for increasing levels of L-DOPA in the plasma of a subject over 24 to 48 hours, comprising administering, about twice per day to about once every other day, an effective dose of a compound of general formula I as defined above to the subject.

According to another aspect of the invention there is provided a method for decreasing levels of 3-O-methyl-L-DOPA (3-OMD) in the brain of a subject over 24 to 48 hours, comprising administering, about twice per day to about once every other day, an effective dose of a compound of general formula I as defined above to the subject.

According to another aspect of the invention there is provided a method for decreasing levels of 3-OMD in the plasma of a subject over 24 to 48 hours, comprising administering, about twice per day to about once every other day, an effective dose of a compound of general formula I as defined above to the subject.

According to another aspect of the invention there is provided a method for increasing bioavailability of L-DOPA in the brain of a subject over 24 to 48 hours, comprising administering, about twice per day to about once every other day, an effective dose of a compound of general formula I as defined above to the subject.

According to another aspect of the invention there is provided a method for increasing bioavailability of L-DOPA in the plasma of a subject over 24 to 48 hours, comprising administering, about twice per day to about once every other day, an effective dose of a compound of general formula I as defined above to the subject.

According to a further aspect of the invention, there is provided a pharmaceutical composition adapted for the administration of a compound of general formula I from about twice per day to about once every other day.

The present invention also relates to a package comprising a pharmaceutical composition of a compound of the general formula I in combination with instructions to administer said formulation with a dosing regimen having a dosing periodicity ranging from twice per day to about once every other day.

In one embodiment, the compounds of the general formula I can be prepared by a process wherein a compound of the general formula IIA, IIB or IIC,

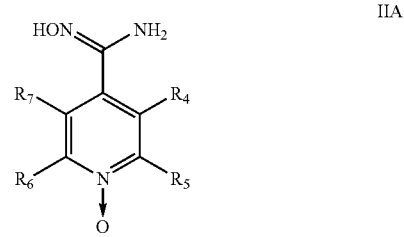

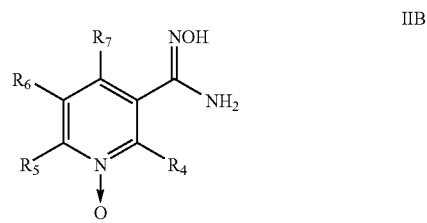

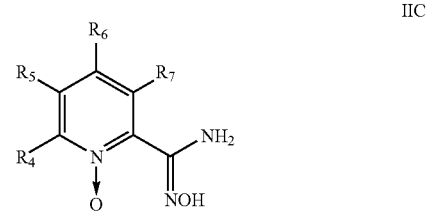

wherein $R_4$, $R_5$, $R_6$ and $R_7$ are as defined in the general formula I, is subjected to a cyclisation reaction comprising condensation and dehydration with a compound of the general formula III,

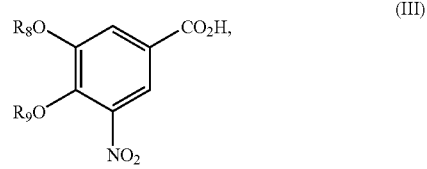

wherein $R_8$ and $R_9$ independently from each other represent hydrogen or suitable protective groups for aromatic hydroxyl groups, under conditions suitable to produce oxadiazole derivatives of formula IVA, IVB or IVC,

IVA

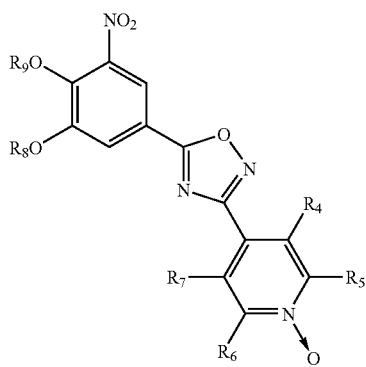

IVB

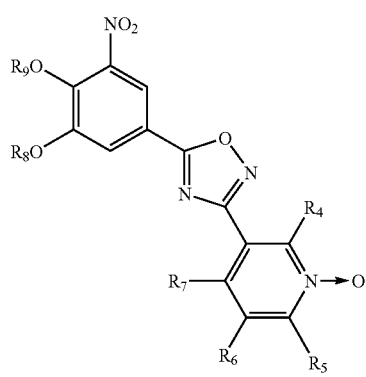

IVC

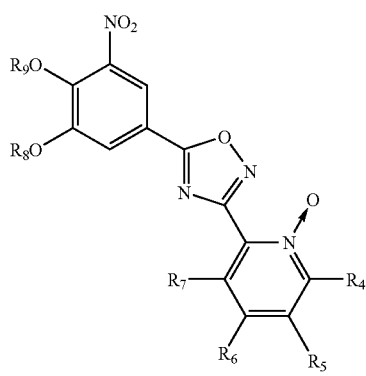

Followed, if required, by removal of the hydroxyl protecting groups to provide the compounds of general formula I.

In another embodiment, the compounds of the general formula I can be prepared by a process wherein a compound of the general formula VA, VB or VC,

VA

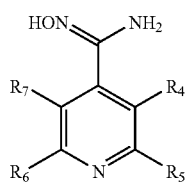

VB

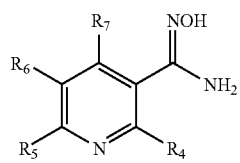

VC

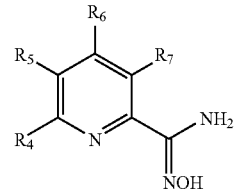

wherein $R_4$, $R_5$, $R_6$ and $R_7$ are as defined in the general formula I, is subjected to a cyclisation reaction comprising condensation and dehydration with a compound of the general formula III under conditions suitable to produce oxadiazole derivatives of formula VIA, VIB or VIC,

VIA

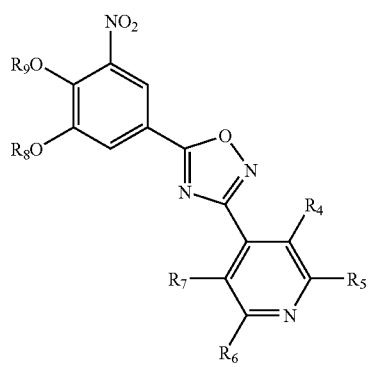

VIB

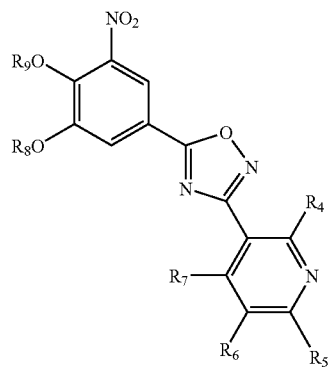

VIC

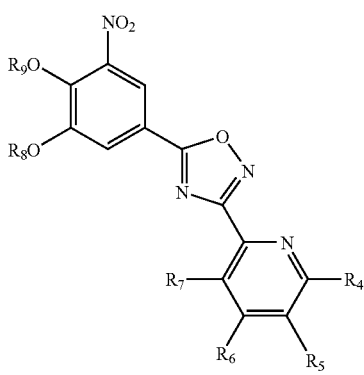

followed by oxidation of the pyridyl nitrogen atom to give a compound according to formula IVA, IVB or IVC as shown above and, if required, the removal of the hydroxyl protecting groups to provide the compounds of general formula I.

Suitable protective groups for aromatic hydroxyl groups are well known in the art. Examples of suitable protective groups for aromatic hydroxyl groups include methyl, ethyl, isopropyl, benzyl, 4-methoxybenzyl, methoxymethyl, benzyloxymethyl, methoxyethoxymethyl, tetrahydropyranyl, phenacyl, allyl, trimethylsilyl, tert-butyldimethylsilyl, benzyloxycarbonyl, tert-butoxycarbonyl, ester, sulphonate, carbamate, phosphinate, acetal and ketal derivatives.

In a preferred embodiment, one of the groups $R_8$ and $R_9$ is hydrogen and the other is methyl. In a particularly preferred embodiment, $R_8$ represents methyl and $R_9$ represents hydrogen.

In an alternative preferred embodiment, the protective groups $R_8$ and $R_9$ are replaced with hydrogen or a group which is hydrolysable under physiological conditions. The protective groups $R_8$ and $R_9$ may be removed independently from each other in separate reaction steps or they may be removed in the same reaction step. Likewise, the insertion of a group which is hydrolysable under physiological conditions may take place either in the same or in a subsequent reaction step.

In the present invention, conditions suitable to produce oxadiazole derivatives comprise conditions which give the oxadiazole derivative in high yield and purity. Preferably, the yield of the desired oxadiazole derivative is at least 70%, more preferably 75 to 99%, even more preferably 80 to 97%, and most preferably 85 to 95%. Preferably, the purity of the desired oxadiazole derivative is at least 90%, more preferably at least 95%, even more preferably at least 99%, and most preferably at least 99.5%. Following the teaching of the present invention the skilled person can routinely determine the most suitable reaction conditions in order to optimize the yield and purity of the oxadiazole. Parameters to be taken into consideration by the skilled person include, but are not limited to, reagents effecting the condensation and dehydration agents, choice of protective groups $R_8$ and $R_9$, solvent system, reaction temperature and reaction time and solubility of reagents.

The compound of general formula III requires activation before the condensation reaction with a compound of formula IIA-IIC or VA-VC. Suitable reagents for activation of the compound of formula III include 1,1-carbonyldiimidazole, thionyl chloride, sulfonylchloride, N,N'-dicyclohexylcarbodiimide, 1-hydroxybenzotriazole and N-(3-dimethylaminopropyl)-N'-ethylcarbodiimide, phosgene, $PCl_3$, $POCl_3$, $PCl_5$, anhydrides, trichlorotriazine and chlorodimethoxytriazine and the like. Particularly preferable are 1,1-carbonyldiimidazole and thionyl chloride. In some cases, the same reagents can be employed to effect the cyclisation step, which consists of condensation and dehydration. Alternative reagents to effect condensation and/or dehydration include pyridine and tetrabutylammonium fluoride.

Preferably the dehydration can be effected by thermal heating of the reaction mixture in conjunction with the aforementioned reagents.

The compound of general formula III can be activated with an excess of a reagent such as thionyl chloride in a suitable solvent or without the need for additional solvent. If preferred, the excess reagent can then be removed, e.g. by distillation, and replaced with a solvent and another reagent such as pyridine to effect the condensation and dehydration steps. Preferred solvent systems for activating the compound of general formula III, and cyclisation with compounds of general formulae IIA-IIC or VA-VC are dipolar aprotic solvents including dimethylformamide, dimethylsulfoxide, dimethylacetamide and N-methylpyrrolidinone. Particularly preferable are dimethylsulfoxide and dimethylacetamide.

Suitable reaction temperatures and reaction times depend on the reactivity of the utilized reagents for effecting condensation and dehydration. Preferably, the reaction temperature is in the range of 0° C. to the boiling point of the utilized solvent system, more preferably in the range of 20 to 150° C., and most preferably in the range of 25 to 120° C. Preferably, the reaction time is in the range of 30 minutes to 24 hours, more preferably in the range of 1 hour to 18 hours, and most preferably 2 to 6 hours.

In an alternative preferred embodiment, the condensation and dehydration reaction is carried out in the presence of an organic or inorganic base. Suitable preferred bases include triethylamine, tributylamine, 2,6-lutidine, N-methylmorpholine, pyridine, imidazole, N-methylimidazole and 4-dimethylaminopyridine. Particularly preferred bases include pyridine, N-methylimidazole and 4-dimethylaminopyridine.

In a preferred embodiment of the present invention, the condensation and dehydration are conducted in two separate reaction steps. In this particular embodiment, different condensation and dehydration agents and solvent systems may be utilized to optimize yield and purity of the obtained product.

In an alternative preferred embodiment of the present invention, the condensation and dehydration are conducted sequentially in the same vessel without isolation of the O-acylated intermediates. In this particular embodiment, the reagents effecting the condensation and dehydration can be the same or different but are preferably identical.

The amount of reagents effecting the condensation and dehydration are not critical. Typical amounts of reagents effecting the condensation and dehydration include at least an amount of 1 mol, preferably 2.1 mol to 5 mol, more preferably 2.2 to 4 mol, and most preferably 2.3 mol to 3 mol, per mol pyridine derivative. In cases in which the reagents effecting the condensation and dehydration also serve as solvent or co-solvent, the excess amount may be much higher.

As mentioned above, in preferred embodiments the invention includes a step in which the nitrogen atom of the pyridyl moiety VIA, VIB or VIC is oxidized under suitable conditions to the corresponding pyridyl-N-oxide derivative IVA, IVB or IVC after the cyclisation reaction.

In the present invention, suitable oxidative conditions to produce the pyridyl-N-oxide comprise conditions which give the pyridyl-N-oxide derivative in high yield and purity. Preferably, the yield of the desired pyridyl-N-oxide derivative is at least 90%, more preferably 92 to 99%, even more preferably 94 to 98%, and most preferably 95 to 97%. Preferably, the purity of the desired pyridyl-N-oxide derivative is at least 90%, more preferably at least 95%, even more preferably at least 99%, and most preferably at least 99.5%. Following the teaching of the present invention the skilled person can routinely determine the most suitable reaction conditions in order to optimize the yield and purity of the pyridyl-N-oxide. Parameters to be taken into consideration by the skilled person include, but are not limited to, oxidizing agent, amount of oxidizing agent, choice of protective groups, solvent system, reaction temperature and reaction time and solubility of reagents.

Preferred oxidizing agents include hydrogen peroxide, $MnO_2$, peracetic acid, trifluoroperacetic acid, t-butylhydroperoxide, m-chloroperoxybenzoic acid, persulfuric acids, Oxone®, urea-hydrogen peroxide complex and trifluoroacetic anhydride, pyridinium chlorochromate and permanganate ions. Particularly preferred is urea-hydrogen peroxide complex and trifluoroacetic anhydride.

The preferred amount of oxidizing agent is in the range of equimolar amounts to a 20-fold excess to the pyridine derivative. Preferably, amount of oxidizing agent is in the range of a 1.2-fold to 10-fold excess, more preferably 1.5-fold to 8-fold excess and most preferably 2-fold to 5-fold excess.

Preferred solvent systems for conducting the oxidation are solvents which are inert to the oxidizing agent. Particularly preferred are halogenated solvents, such as dichloromethane, chloroform, chlorobenzene and carbon tetrachloride, aromatic solvents such as benzene and toluene, alkanes such as cyclohexane and hexane, and ethers such as THF, 1,4-dioxane and tert-butylmethylether.

Suitable reaction temperatures and reaction times depend on the reactivity of the utilized oxidizing agent. Preferably, the reaction temperature is in the range of 0° C. to the boiling point of the utilized solvent system, more preferably in the range of 20 to 100° C., and most preferably in the range of 40 to 80° C. Preferably, the reaction time is in the range of 30 minutes to 24 hours, more preferably in the range of 1 hour to 18 hours, and most preferably 2 to 6 hours.

The oxidation of the pyridyl nitrogen atom can be carried out at any stage of the process of preparation of compounds according to the general formula I. Preferably, the oxidation is conducted before formation of the compounds of formulae IIA-IIC, or alternatively after formation of the oxadiazole ring as in compounds of formulae VIA-VIC.

In another aspect of the invention, compounds of formula IIA, IIB or IIC are prepared by reacting compounds of the general formula VIIA, VIIB or VIIC,

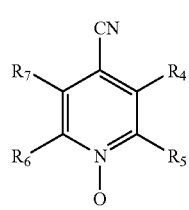

VIIA

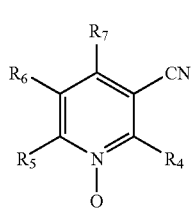

VIIB

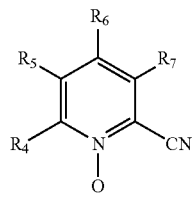

VIIC with hydroxylamine in the presence of a chelating agent under suitable reaction conditions.

In another aspect of the invention, compounds of formula VA, VB or VC are prepared by reacting compounds of the general formula VIIIA, VIIIB or VIIIC,

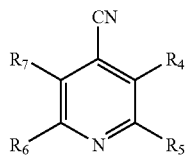

VIIIA

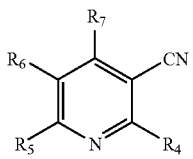

VIIIB

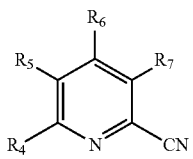

VIIIC with hydroxylamine in the presence of a chelating agent under suitable reaction conditions.

In the present invention, suitable reaction conditions of the above reactions comprise conditions which give the amidoxime derivative in high yield and purity. Preferably, the yield of the desired amidoxime derivative is at least 70%, more preferably 72 to 95%, even more preferably 75 to 90%, and most preferably 78 to 85%. Preferably, the purity of the desired amidoxime derivative is at least 90%, more preferably at least 95%, even more preferably at least 96%, and most preferably at least 97%. Following the teaching of the present invention the skilled person can routinely determine the most suitable reaction conditions in order to optimize the yield and purity of the amidoxime. Parameters to be taken into consideration by the skilled person include, but are not limited to, amount of hydroxylamine, choice of catalyst, nature of substituents $R_4$-$R_7$, solvent system, reaction temperature and reaction time and solubility of reagents.

The preferred amount of hydroxylamine is in the range of equimolar amounts to a 50-fold excess to the pyridine derivative. Preferably, the amount of hydroxylamine is in the range of a 1.2-fold to 20-fold excess, more preferably 1.5-fold to 10-fold excess and most preferably 3-fold to 5-fold excess.

Preferred chelating agents include 8-hydroxyquinoline, ortho-phenanthroline and hydrates and derivatives thereof. The preferred amount of chelating agent is in the range 0.1-10 mol %, more preferably 0.5-5 mol %, more preferably 0.75-3 mol % and most preferably 1-1.5 mol %.

The solvent system is not particularly limited and includes water, alcohols such as methanol, ethanol or isopropanol, ethers such as THF or 1,4-dioxane, and dipolar aprotic solvents, such as dimethylsulfoxide and the like or mixtures of these solvents.

Preferably, the reaction temperature is in the range of 0° C. to the boiling point of the utilized solvent system, more preferably in the range of 20 to 100° C., and most preferably in the range of 40 to 80° C. Preferably, the reaction time is in the range of 30 minutes to 24 hours, more preferably in the range of 1 hour to 18 hours, and most preferably 2 to 8 hours.

The bioavailability, bioactivity, safety profile and other related properties known in the art (e.g. blood-brain-barrier permeability) of the compounds of general formula I can be routinely optimized by the skilled person on basis of the teaching of the present application by varying substituents $R_1$-$R_7$ of the above general formula I in order to obtain a desirable balanced mix of properties.

The compounds of general formula I may also be present in the form of pharmacologically acceptable salts thereof. Suitable pharmaceutically acceptable counter ions are known to the art.

It is also possible to use prodrugs of compounds of the general formula I in order to alter the therapeutic profile of the active compound.

Materials and Methods

Assay of COMT Activity

Livers from 60 day old male Wistar rats weighing 240-260 g (Harlan-Interfauna Ibérica, Barcelona, Spain), kept two per cage under controlled environmental conditions (12 h light/dark cycle and room temperature 24° C.) were used in all experiments. After decapitation, the organs were immediately removed and homogenised in 5 mM phosphate buffer of pH 7.8. COMT activity was evaluated by the ability to methylate adrenaline to metanephrine. Aliquots of 0.5 ml of liver homogenates were preincubated for 20 min with 0.4 ml of phosphate buffer (5 mM); thereafter, the reaction mixture was incubated for 15 min with epinephrine (2000 µM; 0.1 ml) in the presence of a saturating concentration of S-adenosyl-L-methionine (500 µM), the methyl donor; the incubation medium contained also pargyline (100 µM), $MgCl_2$ (100 µM) and EGTA (1 mM). The preincubation and incubation were carried out at 37° C. under conditions of light protection with continuous shaking and without oxygenation.

In experiments designed to evaluate the oral bioavailability of test substances, compounds were given by gastric tube to overnight fasted rats. Thereafter, at defined intervals, animals were killed by decapitation and livers removed and used to determine COMT activity as described above. At the end of the incubation period (5 min) the tubes were transferred to ice and the reaction was stopped by the addition of 200 µl of 2 M perchloric acid. The samples were then centrifuged (200×g, 4 min, 4° C.), and 500 µl aliquots of the supernatant, filtered on 0.22 µm pore size Spin-X filter tubes (Costar) were used for the assay of metanephrine. The assay of metanephrine was carried out by means of high pressure liquid chromatography with electrochemical detection. The lower limits for detection of metanephrine ranged from 350 to 500 fmol (0.5 to 1.0 µmol/mg protein/h).

Levels of L-DOPA and its Derivatives in Whole Brain and Plasma

Rats fasted overnight were administered orally with tolcapone and compounds of general formula I (3 mg/kg) or vehicle (0.5% carboxymethylcellulose, 4 ml/kg). One, 6 or 23 h later, rats were administered orally with L-DOPA (12 mg/kg) plus benserazide (3 mg/kg) or with vehicle (0.5% carboxymethylcellulose, 4 ml/kg). One hour later rats were anaesthetized with sodium pentobarbitone (60 mg/kg, i.p.), blood was collected through the vena cava and the whole brain was quickly removed. Brains were stored in perchloric acid 0.2 M for subsequent assay of L-DOPA, 3-O-methyl-L-DOPA, dopamine, DOPAC and HVA. Blood samples were centrifuged for 15 min at 3,000 g (4° C.) and the plasma samples were stored at −80° C. till the assay of L-DOPA and 3-O-methyl-L-DOPA. All animals interventions were performed in accordance with the European Directive number 86/609, and the rules of the "Guide for the Care and Use of Laboratory Animals", 7th edition, 1996, Institute for Laboratory Animal Research (ILAR), Washington, D.C.

Assay of L-DOPA and Catechol Derivatives

L-DOPA, 3-O-methyl-L-DOPA, dopamine and metabolites (DOPAC and HVA) in dialysate samples were assayed by HPLC with electrochemical detection, as previously described (Soares-da-Silva et al., Brain Res. 2000; 863:293-297). In brief, aliquots of 20 µl were injected into the chromatograph. The chromatographic system consisted of a pump (Gilson 307) and a stainless steel 5 µm ODS2 column (Biophase; Bioanalytical Systems, West Lafayette, Ind.) of 25 cm length and 4.6 mm diameter; samples were injected by means of an automatic sample injector (Gilson 231) connected to a Gilson dilutor (Gilson 401). The mobile phase was a degassed solution of citric acid 0.1 mM; sodium octylsulphate 0.5 mM; sodium acetate 0.1 M; $Na_2EDTA$ 0.17 mM; dibutylamine 1 mM and methanol (10% v/v), adjusted to pH 3.5 with PCA 2 M and pumped at a rate of 1.0 ml min$^{-1}$. The detection was carried out electrochemically with a glassy carbon electrode, an Ag/AgCl reference electrode and an amperometric detector (Gilson 142); the detector cell was operated at 0.75 V. The current produced was monitored using the Gilson Unipoint HPLC software. The lower limit of detection of dopamine, DOPAC and HVA ranged from 350 to 1000 fmol.

RESULTS

Figure 1:
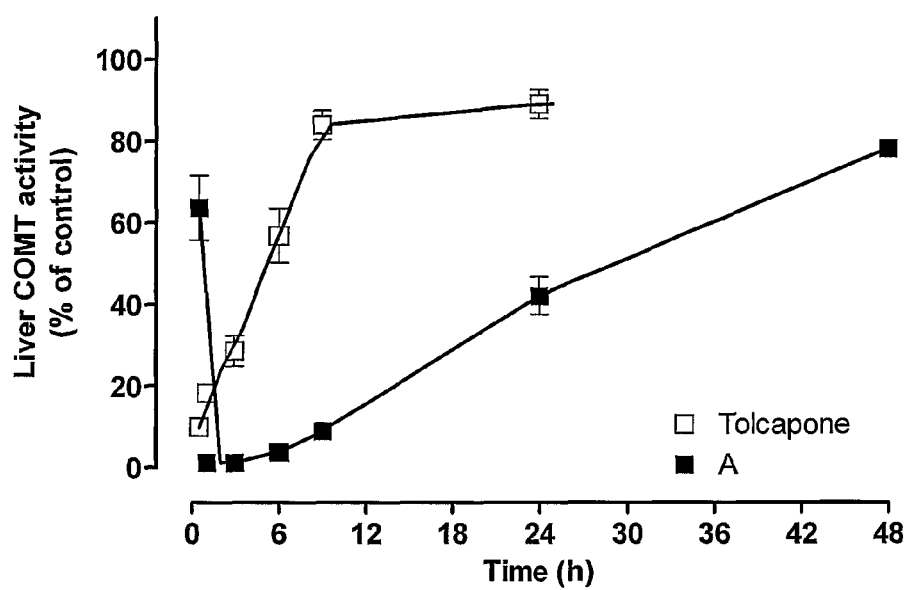
FIG. 1. Effect of compound A and tolcapone (3 mg/kg) on liver COMT activity at 0.5, 1, 3, 6, 9, 24 and 48 h after the administration of the COMT inhibitor. Symbols represent means±SEM of 5 experiments per group. Significantly different from corresponding controls values (*P<0.05).

Compounds of general formula I, e.g. compound A, were found to be potent inhibitors of liver COMT, the maximal inhibitory effect being achieved within 60 min after their oral administration (FIG. 1). The maximal inhibitory effect of tolcapone was observed within 30 min after administration (FIG. 1). Nine hours after administration, tolcapone produces minimal inhibitory effects, whereas compounds of general formula I, e.g. compound A, continues to inhibit COMT activity at 90% of control levels (FIG. 1). As shown in FIG. 1, even at 24 hours after administration, compounds of general formula I, e.g. compound A, are capable of inhibiting liver COMT at 60% of controls levels, whereas tolcapone was again almost devoid of COMT inhibitory properties.

Figure 2:
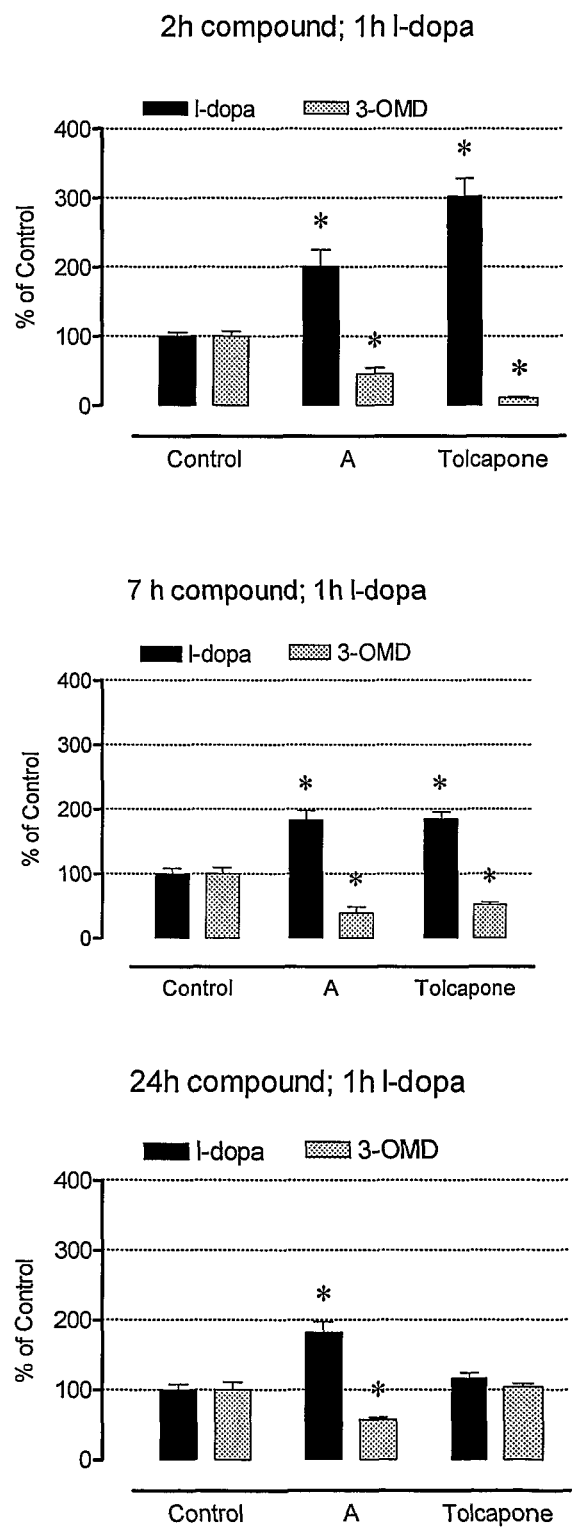
FIG. 2. Effect of compound A and tolcapone (3 mg/kg) on plasma levels of L-DOPA and 3-O-methyl-L-DOPA in rats treated with L-DOPA (12 mg/kg) plus benserazide (3 mg/kg), at 2, 7 and 24 h after the administration of the COMT inhibitor. Columns represent means±SEM of 5 experiments per group. Significantly different from corresponding controls values (*P<0.05).

FIG. 2 shows levels of L-DOPA and 3-O-methyl-L-DOPA in plasma of rats treated with L-DOPA plus benserazide at 2, 7 and 24 h after the administration of tolcapone and compounds of general formula I, e.g. compound A, (3 mg/kg). L-DOPA plus benserazide were administered 1 h before collection of blood samples. This time-point was chosen because it represented the $T_{max}$ for L-DOPA. As can be observed, compounds of general formula I, e.g. compound A, produced significant increases in plasma L-DOPA accompanied by marked decrease in circulating 3-O-methyl-L-DOPA, this being identical at all pre-treatment times with compounds of general formula I, e.g. compound A, (1, 7 and 24 h). Plasma levels of L-DOPA and 3-O-methyl-L-DOPA are not affected when tolcapone was administered 24 h in advance. Significant changes on L-DOPA and 3-O-methyl-L-DOPA plasma levels by tolcapone were only observed at shorter time points 2 and 7 h after the administration of the compound.

Figure 3:
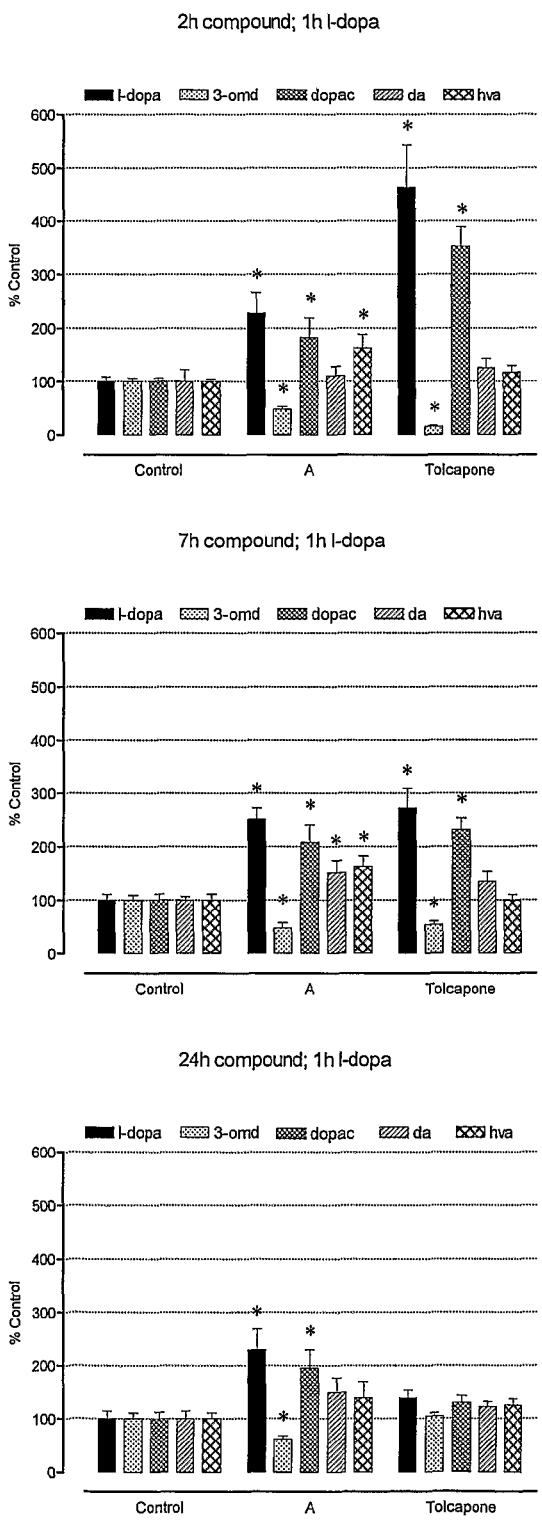
FIG. 3. Effect of compound A and tolcapone (3 mg/kg) on brain levels of L-DOPA, 3-O-methyl-L-DOPA, dopamine, DOPAC and HVA in rats treated with L-DOPA (12 mg/kg) plus benserazide (3 mg/kg), at 2, 7 and 24 h after the administration of the COMT inhibitor. Columns represent means±SEM of 5 experiments per group. Significantly different from corresponding controls values (*P<0.05).

FIG. 3 shows levels of L-DOPA, 3-O-methyl-L-DOPA, DOPAC, dopamine and HVA in the brain of rats treated with L-DOPA plus benserazide at 2, 7 and 24 h after the administration of tolcapone and compounds of general formula I, e.g. compound A, (3 mg/kg). L-DOPA plus benserazide were administered 1 h before collection of brain samples. This time-point was chosen because it represented the $T_{max}$ for L-DOPA. As can be observed, compounds of general formula I, e.g. compound A, produced significant increases in brain L-DOPA, dopamine and DOPAC accompanied by marked decrease in brain 3-O-methyl-L-DOPA, this being identical at all pre-treatment times with compounds of general formula I, e.g. compound A, (1, 7 and 24 h). Brain levels of L-DOPA, dopamine, DOPAC and 3-O-methyl-L-DOPA were not affected when tolcapone was administered 24 h in advance. Significant changes to L-DOPA, dopamine, DOPAC and 3-O-methyl-L-DOPA brain levels by tolcapone were only observed at 2 and 7 h after the administration of the compound.

The invention will now be described with reference to the following example of preparation, which is not intended to limit the invention in any way.

EXAMPLE 1

Preparation of Compound A (5-[3-(2,5-Dichloro-4,6-dimethyl-1-oxy-pyridin-3-yl)-[1,2,4]oxadiazol-5-yl]-3-nitrobenzene-1,2-diol)

a) To a stirred solution of 3,4-dibenzyloxy-5-nitrobenzoic acid (0.50 g, 1.318 mmol) in dimethylformamide (5 mL) at room temperature was added 1,1-carbonyldiimidazole (0.24 g, 1.48 mmol) in one portion. After stirring for ninety minutes, 2,5-dichloro-N'-hydroxy-4,6-dimethylnicotinimidamide (0.40 g, 1.71 mmol) was added in one portion. The resulting mixture was stirred at 135° C. for five hours and then at room temperature overnight. The reaction mixture was poured onto ice-2 N HCl (100 mL) and the resulting precipitate was filtered off, washed with water and dried in air. Recrystallisation from isopropanol gave a pale yellow solid (0.55 g, 72%).

b) To a stirred solution of the solid obtained above (0.50 g, 0.866 mmol) in dichloromethane (20 mL) was added urea-hydrogen peroxide addition complex (0.41 g, 4.36 mmol) in one portion. The mixture was cooled in an ice-water batch and trifluoroacetic anhydride (0.73 g, 3.48 mmol) was added dropwise. The reaction mixture was allowed to stir at room temperature overnight whereupon insoluble material was filtered off. The filtrate was washed with water and brine, dried over anhydrous magnesium sulphate, filtered and evaporated. The residue was crystallised from isopropanol to give a pale yellow solid (0.35 g, 68%).

c) To a stirred solution of the solid obtained above (0.30 g, 0.5 mmol) in dichloromethane (10 mL) at −78° C. under argon was added boron tribromide (0.38 g, 1.5 mmol) dropwise. The resulting purple suspension was allowed to stir at room temperature for one hour, then cooled again to −78° C. and carefully quenched by the addition of water. After stirring at room temperature for one hour, the precipitate was filtered off, washed with water and dried at 50° C. under vacuum to afford the desired compound as yellow crystals (0.18 g, 86%) of m.p. 237-240° C.

EXAMPLE 2

Pharmaceutical Formulation

Suitable exemplary pharmaceutical formulations are prepared according to the following specifications:

Capsule:

| | |
|---|---|
| Compound A | 15.0% |
| Lactose monohydrate | 43.0% |
| Microcrystalline cellulose | 30.0% |
| Povidone | 4.0% |
| Croscarmellose sodium | 5.0% |
| Talc | 2.0% |
| Magnesium stearate | 1.0% |

Capsule:

| | |
|---|---|
| Compound A | 15.0% |
| Microcrystalline cellulose | 72.5% |
| Ethylcellulose | 5.0% |
| Sodium starch glycolate | 6.0% |
| Colloidal Silicon Dioxide | 0.5% |
| Magnesium stearate | 1.0% |

Tablet:

| | |
|---|---|
| Compound A | 20.0% |
| Microcrystalline cellulose | 25.0% |
| Calcium Phosphate, dibasic dihydrate | 40.0% |
| Povidone | 6.0% |
| Croscarmellose sodium | 6.0% |
| Talc | 2.0% |
| Magnesium stearate | 1.0% |

EXAMPLE 3

Dosing Regimen

Patients suffering from a movement disorder and who are on L-DOPA therapy are treated with tablets containing 50 mg of compound of the general formula I. A significant improvement in the clinical picture is evidenced.

The invention claimed is:

1. Method of treating a movement disorder in a patient in need thereof comprising administering to the patient about twice every day to about once every other day a pharmacologically effective dose of 5-[3-(2,5-dichloro-4,6-dimethyl-1-oxy-pyridin-3-yl)-[1,2,4]oxadiazol-5-yl]-3-nitrobenzene-1,2-diol or a pharmacologically acceptable salt thereof,
   wherein the movement disorder is selected from Parkinson's disease, dystonia, dyskinesia, and extrapyramidal syndromes.

2. Method as claimed in claim 1 wherein the administration is once daily.

3. Method as claimed in claim 1 wherein the administration is twice daily.

4. Method as claimed in claim 1 wherein the administration is once every other day.

5. Method according to claim 1, wherein the movement disorder is treatable by L-DOPA and/or AADC therapy.

6. Method as claimed in claim 1 wherein the movement disorder is Parkinson's disease.

7. Method according to claim 1 wherein the method further comprises the step of administering L-DOPA to the patient.

8. Method according to claim 1 wherein the method further comprises the step of administering an AADC inhibitor to the patient.

9. Method according to claim 1 wherein the patient is receiving therapy with L-DOPA or an AADC inhibitor or both L-DOPA and an AADC inhibitor.

10. Method according to claim 1 wherein the method further comprises the step of administering of L-DOPA and an AADC inhibitor to the patient either concomitantly or sequentially with the compound as defined in claim 1.

11. Method according to claim 1 wherein the method further comprises the step of administering of L-DOPA and an AADC inhibitor to the patient separately with the compound as defined in claim 1.

12. Method according to claim 1 wherein the effective daily doses of compounds of formula I are in the range of 1 to 1000 mg/day.

13. Method according to claim 1 wherein the effective daily doses of compounds of formula I are in the range of 2 to 500 mg/day.

14. Method according to claim 1 wherein the effective daily doses of compounds of formula I are in the range of 3 to 250 mg/day.

15. Method according to claim 1 wherein the effective daily doses of compounds of formula I are in the range of 5 to 100 mg/day.

16. Method according to claim 1 wherein the administration is in the morning, mid-day, noon, afternoon, evening, or midnight.

17. Method according to claim 1 wherein the administration is in the evening.

* * * * *

UNITED STATES PATENT AND TRADEMARK OFFICE
CERTIFICATE OF CORRECTION

| | | |
|---|---|---|
| PATENT NO. | : 8,524,746 B2 | Page 1 of 1 |
| APPLICATION NO. | : 12/524848 | |
| DATED | : September 3, 2013 | |
| INVENTOR(S) | : David Alexander Learmonth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 643 days.

Signed and Sealed this
Twenty-second Day of April, 2014

Michelle K. Lee
*Deputy Director of the United States Patent and Trademark Office*